(12) United States Patent  
Patel et al.

(10) Patent No.: US 11,578,025 B2  
(45) Date of Patent: Feb. 14, 2023

(54) PROCESSES FOR THE PREPARATION OF ZUCLOMIPHENE INTERMEDIATES

(71) Applicant: Apotex Inc., Toronto (CA)

(72) Inventors: Dineshkumar Patel, Brantford (CA); Avedis Karadeolian, Brantford (CA); Fabio E. S. Souza, Brantford (CA); Allan W. Rey, Brantford (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 17/503,727

(22) Filed: Oct. 18, 2021

(65) Prior Publication Data

US 2022/0119331 A1  Apr. 21, 2022

Related U.S. Application Data

(60) Provisional application No. 63/093,509, filed on Oct. 19, 2020.

(51) Int. Cl.
```
C07C 37/62    (2006.01)
B01J 23/755   (2006.01)
C07C 17/263   (2006.01)
C07C 37/14    (2006.01)
```

(52) U.S. Cl.
CPC ............. *C07C 37/62* (2013.01); *B01J 23/755* (2013.01); *C07C 17/2632* (2013.01); *C07C 37/14* (2013.01)

(58) Field of Classification Search
None
See application file for complete search history.

(56) References Cited

U.S. PATENT DOCUMENTS

| | | | |
|---|---|---|---|
| 2,914,563 | A | 11/1959 | Allen et al. |
| 3,848,030 | A | 11/1974 | Viterbo et al. |
| 9,428,442 | B2 | 8/2016 | Serafini et al. |
| 9,914,696 | B2 | 3/2018 | Podolski et al. |
| 11,046,638 | B2 | 6/2021 | Karadeolian et al. |
| 2015/0202167 | A1 | 7/2015 | Podolski et al. |

(Continued)

FOREIGN PATENT DOCUMENTS

WO  2014031177 A1  2/2014

OTHER PUBLICATIONS

Xue, F. et al. "Nickel-Catalyzed Three-Component Domino Reactions of Aryl Grignard Reagents, Alkynes, and Aryl Halides Producing Tetrasubstituted Alkenes" J. Am. Chem. Soc. 2015, 137, 3189-3192 (Year: 2015).*

(Continued)

*Primary Examiner* — Medhanit W Bahta
(74) *Attorney, Agent, or Firm* — The Webb Law Firm

(57) ABSTRACT

The present invention provides continuous flow processes for the preparation of the compound of Formula (2-A), an intermediate used in the preparation of zuclomiphene or a salt thereof.

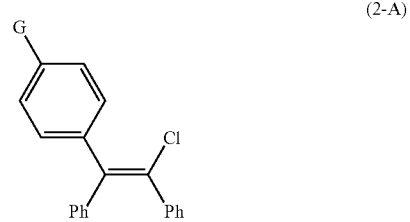

(2-A)

16 Claims, 1 Drawing Sheet

(56) References Cited

U.S. PATENT DOCUMENTS

2021/0147337 A1* 5/2021 Karadeolian .......... B01J 23/755
2021/0147338 A1* 5/2021 Raheem .................. C07C 55/06

OTHER PUBLICATIONS

Ming, J. et al. "Rhodium-Catalyzed Arylzincation of Alkynes: Ligand Control of 1,4-Migration Selectivity" Org. Lett. 2018, 20, 6188-6192 (Year: 2018).*

Xie, M. et al. "Regio- and stereospecific synthesis of vinyl halides via carbozincation of acetylenic sulfones followed by halogenation" Journal of Organometallic Chemistry 694 (2009) 2258-2262 (Year: 2009).*

Al-Hassan, "Synthesis of Clomid Using Palladium-Catalyzed Cross-Coupling", Syn.Commun., 1987, pp. 1787-1796, vol. 17:15.

Crenshaw et al., "Synthesis of Trisubstituted Vinyl Chlorides", J. Org. Chem. 1983, pp. 2782-2784, vol. 48:16.

Dolginova et al., "Synthesis and Biological Study of the cis- and trans- Isomers of Clomiphene Citrate and Some Intermediates of Its Sythesis", Pharm. Chem. J., 1984, pp. 758-764, vol. 11.

Karadeolian et al, "Processes for the Preparation of Zuclomiphene and Intermediates Thereof", U.S. Appl. No. 62/935,107, filed Nov. 14, 2019, Corresponds to U.S. Pat. No. 11,046,638.

Palopoli et al., "Substituted Aminoalkoxytriarylhaloethylenes", J. Med. Chem., 1967, pp. 84-86, vol. 10:1.

* cited by examiner

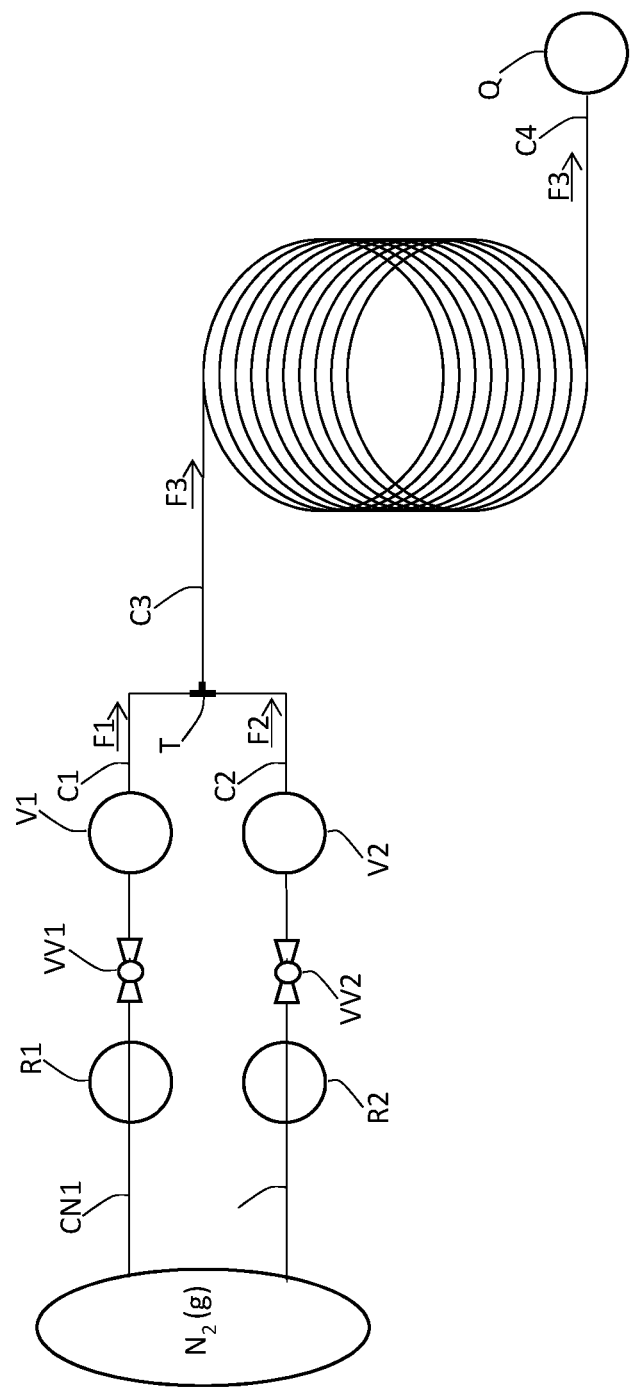

PROCESSES FOR THE PREPARATION OF ZUCLOMIPHENE INTERMEDIATES

CROSS-REFERENCE TO RELATED APPLICATION

This application claims priority to U.S. Provisional Patent Application No. 63/093,509 filed Oct. 19, 2020, the disclosure of which is hereby incorporated by reference in its entirety.

BACKGROUND OF THE INVENTION

Field of the Invention

The present invention relates to processes for the preparation of intermediates useful in the preparation of zuclomiphene.

Description of Related Art

Clomid®, a drug initially approved by the United States Food and Drug Association in 1967 as an ovulatory stimulant, is an isomeric mixture of the citrate salts of cis-clomiphene (Z-clomiphene or 'zuclomiphene', (1-A)) and trans-clomiphene (E-clomiphene or 'enclomiphene', (1-B)) containing between 30% and 50% of the cis-isomer. Pure cis-isomer zuclomiphene (1-A), or (2-[4-[(Z)-2-chloro-1,2-diphenylethenyl]phenoxy]-N,N-diethylethanamine), in the form of the citrate salt, is currently undergoing evaluation in clinical trials in the United States to treat hot flashes experienced by male patients with advanced prostate cancer undergoing androgen deprivation therapy (ADT).

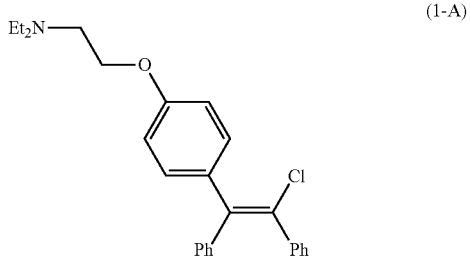
(1-A)

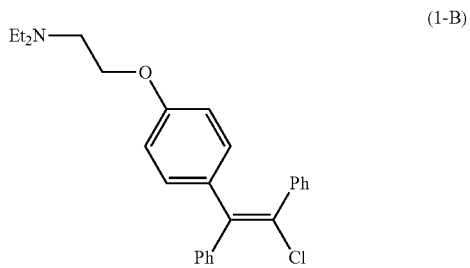
(1-B)

A process for the preparation of a series of substituted aminoalkoxytriarylhaloethylenes, which includes clomiphene, is disclosed in Palopoli et al. *J. Med. Chem.* 1967, 10 (1), 84-6, which is depicted in Scheme 1. Triarylethylene (D) 5514574. DOCX 1 is obtained by reaction of benzylmagnesium bromide (B) with aminoethoxy-substituted diphenyl ketone (A), followed by dehydration of alcohol (C). Chlorination of triarylethylene (D) using a solution of chlorine in carbon tetrachloride followed by salt formation with citric acid affords an unspecified ratio of clomiphene isomers (1) as dihydrogen citrate salts. Further conversion of the isomeric salt mixture to the corresponding hydrochloride salts followed by repeated fractional crystallization affords isolated isomers zuclomiphene (1-A) hydrochloride and enclomiphene (1-B) hydrochloride.

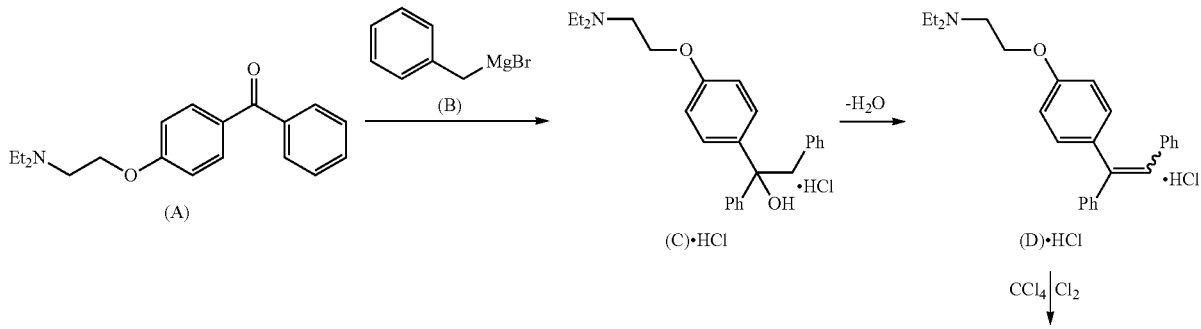

Scheme 1 (Prior Art)

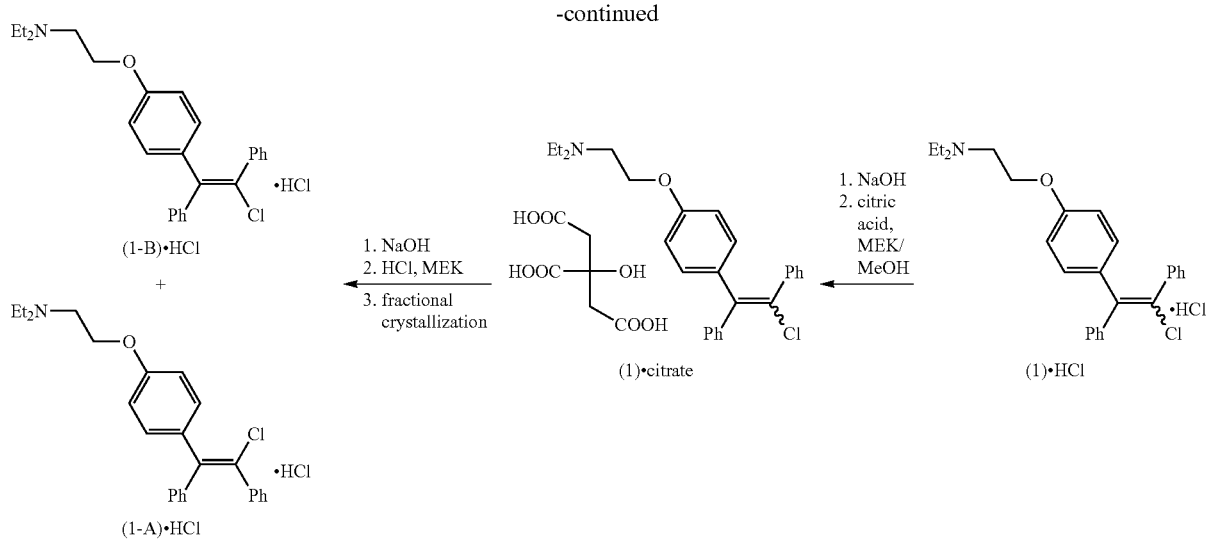

A number of other procedures reported for the preparation of clomiphene, including those described in U.S. Pat. No. 2,914,563 A, WO 2014/031177 A1, U.S. Pat. No. 9,428,442 B2, and U.S. Pat. No. 9,914,696 B2, follow the same basic synthetic approach comprising Grignard addition of benzylmagnesium bromide to substituted diaryl ketone (A), followed by dehydration and chlorination of the corresponding alcohol (C).

The major drawback of applying this synthetic approach to the preparation of zuclomiphene is that the resulting clomiphene that is provided is an isomeric mixture that is typically enriched in the E-isomer enclomiphene. According to U.S. Pat. No. 9,428,442 B2 for example, clomiphene afforded by treatment of triarylethylene (D) hydrochloride with N-chlorosuccinimide as chlorinating agent comprises only 30 to 50% of the Z-isomer zuclomiphene.

A second synthetic method for the preparation of clomiphene is described in Crenshaw et al. *J. Org. Chem.*, 1983, 48 (16), 2782-4. In this process, which is exemplified in Scheme 2, chlorobenzylphosphonate (E) is lithiated and subsequently reacted with aminoethoxy-substituted diphenyl ketone (A) in a Horner-Emmons-type manner to directly afford a clomiphene mixture (1) comprising 47% zuclomiphene and 53% enclomiphene. As above, this method provides clomiphene enriched in the undesired isomer.

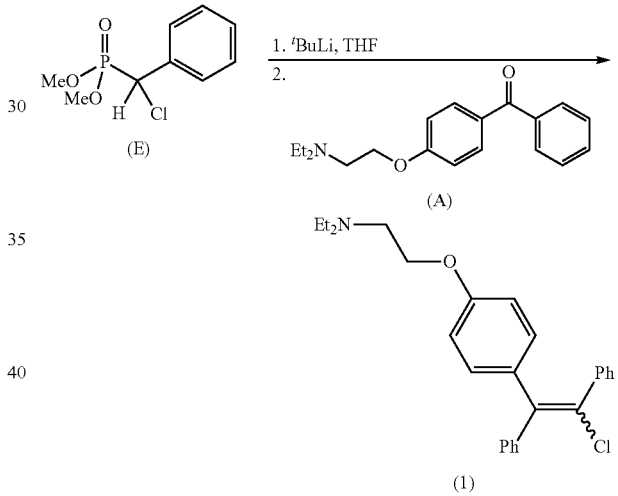

In Al-hassan et al. *Synth. Commun.*, 1987, 17 (15), 1787-1796, clomiphene is prepared via a third method comprising hydroalumination of diphenylacetylene (F) followed by palladium-catalyzed cross-coupling as shown in Scheme 3. In this method, diphenylacetylene (F) undergoes hydroalumination to afford vinylalane (G) which is used as is or is cleaved with iodine to afford vinyl iodide (H). Subsequent cross-coupling of either vinylalane (G) with p-bromoanisole or of vinyl iodide (H) with (p-methoxyphenyl)zinc chloride affords methoxyaryl compound (I). Demethylation of (I) with sodium ethylthiolate followed by alkylation of the resulting phenoxide with 2-(N,N-diethylamino)ethyl chloride affords triarylethylene (D) which is chlorinated by treatment with N-chlorosuccinimide to afford clomiphene (1). The final step of this process comprises an analogous chlorination of triarylethylene (D) that is used in Palopoli et al. As such, this method also suffers from the same lack of stereo control mentioned above.

Scheme 3 (Prior Art)

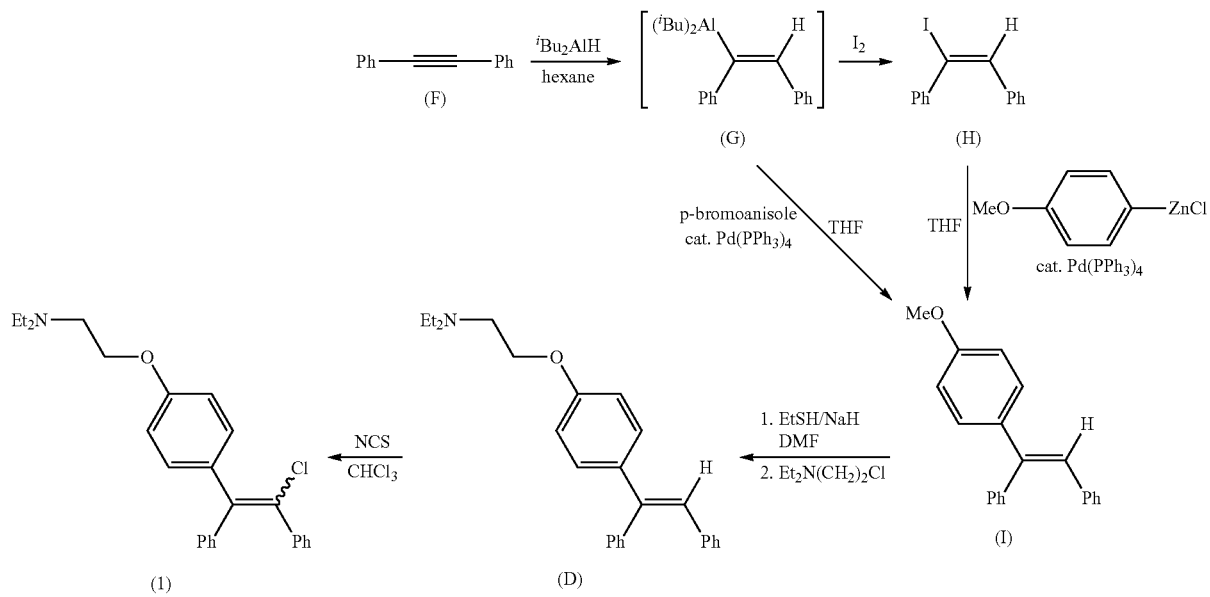

Retrieving pure zuclomiphene from an isomeric mixture that is obtained from the reported methods can be accomplished by fractional crystallization of zuclomiphene free form or a salt thereof as described in, for example, U.S. Pat. No. 3,848,030 A, Dolginova et al. *Pharm. Chem. J.* 1984, 11, 758-764 and Palopoli et al. *J. Med. Chem.* 1967, 10 (1), 84-6. The maximum recovery of zuclomiphene by fractional crystallization is limited by the isomeric composition of clomiphene established by the reported synthetic methods, which is generally balanced in favour of the undesirable enclomiphene isomer. As a result, the overall yield of known methods for the preparation of zuclomiphene is low.

Owing to the drawbacks of the existing processes, there remains a need for improved processes for the preparation of zuclomiphene (1-A), and the intermediates used in such preparations, that are more amenable to scale-up and use on a commercial scale.

SUMMARY OF THE INVENTION

The present invention provides improved processes for the preparation of the compound of Formula (1-A) and intermediates thereof that employ continuous flow technology.

Development of the processes of the present invention followed, in part, from the development of the process described in U.S. Patent Application No. 62/935,107, incorporated by reference herein, and shown in Scheme 4. In this process, zuclomiphene (1-A), or a salt thereof, is prepared by a nickel-catalyzed carbometallation of diphenylacetylene (4) with the compound of Formula (3), followed by chlorination to afford either zuclomiphene (1-A), or the intermediate of Formula (2-A), which can be further reacted to convert moiety G to the desired (N,N-diethylamino)ethoxy group of zuclomiphene (1-A).

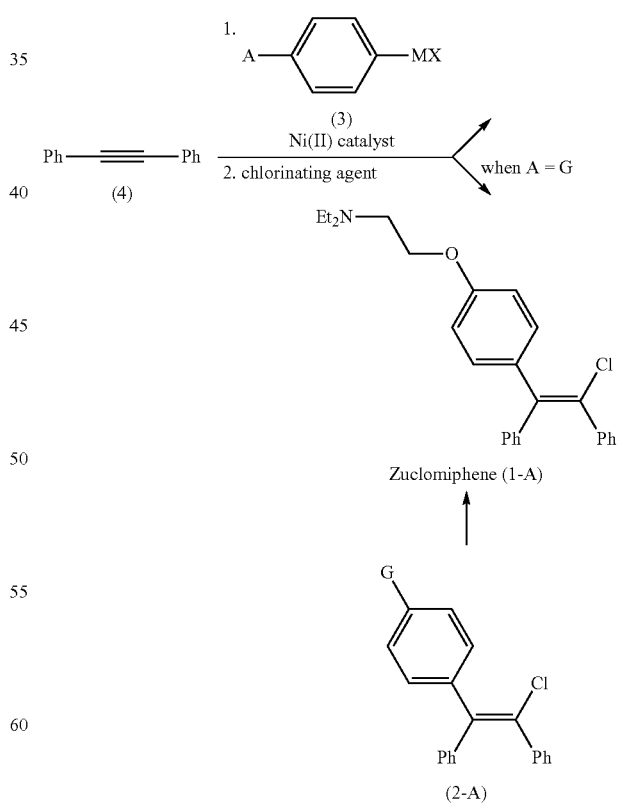

wherein
A is —OCH$_2$CH$_2$NEt$_2$ or G;
G is OPG or X$^1$;

PG is an alcohol protecting group;

M is zinc or magnesium; and

X and $X^1$ are independent halide groups.

It was discovered that embodiments of this process wherein MX in the compound of Formula (3) is MgBr and A is fluoride led to formation of more than 15% of a pervasive brominated impurity of Formula (IMP) in the chlorination step, which is difficult to remove downstream.

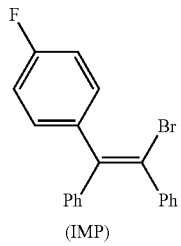

(IMP)

As a result, process modifications and/or additional purification operations were required to lower the impurity levels in the compound of Formula (1-A) to acceptable levels. Methods were therefore desired to control the formation of impurity (IMP), goals that were achieved with the continuous flow process described herein. In some examples, the brominated impurity present in the mixture of product after the chlorination step is less than about 10 percent, or about 2 to about 10 percent, or about 3 to about 7 percent, or about 4 to about 6 percent, as determined by HPLC, based upon the relative area count of the total mixture of product after the chlorination step.

The present invention provides a process for the preparation of zuclomiphene (1-A) as shown in Scheme 5 comprising chlorination of the intermediate compound of Formula (X) in continuous flow. In preferred embodiments of the present invention, formation of bromination impurity (IMP) is suppressed, resulting in fewer downstream purification cycles, reduced solvent waste, and higher yields of zuclomiphene (1-A).

Scheme 5

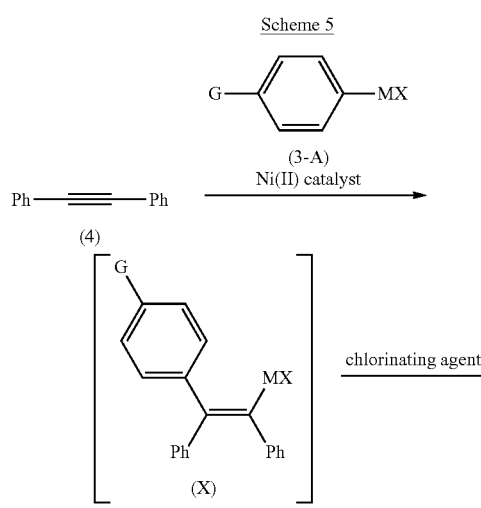

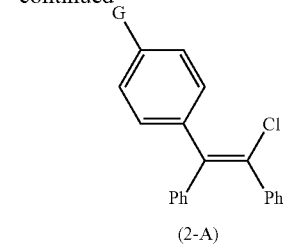

(2-A)

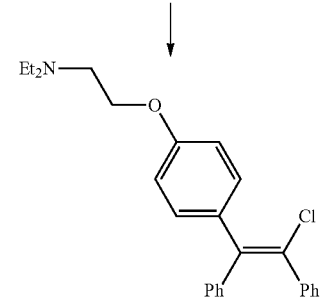

Zuclomiphene (1-A)

wherein
G is OPG or $X^1$;
PG is an alcohol protecting group;
M is zinc or magnesium; and
X and $X^1$ are independent halide groups.

Accordingly, in a first aspect of the present invention, there is provided a continuous flow process for the preparation of a compound of Formula (2-A):

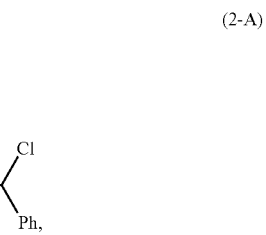

(2-A)

comprising contacting a continuous flow (F1) of the compound of Formula (X):

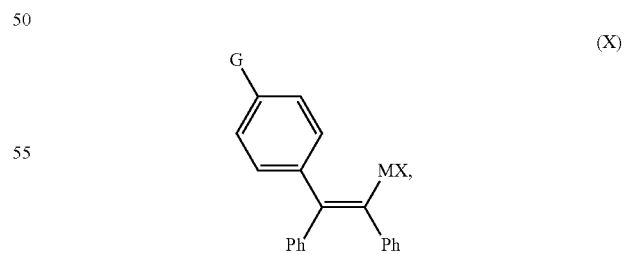

(X)

in a solvent (S1), with a continuous flow (F2) of a chlorinating agent in a solvent (S2), to provide continuous flow (F3) containing the compound of Formula (2-A), wherein G is OPG or $X^1$; PG is an alcohol protecting group; M is zinc or magnesium; and X and $X^1$ are independent halide groups.

In a preferred embodiment of the first aspect, the continuous flow (F1) of the compound of Formula (X) comprises a reaction mixture resulting from reacting diphenylacetylene, in the presence of a nickel(II) catalyst and solvent (S1), with a compound of Formula (3-A):

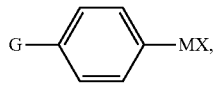

(3-A)

wherein G is OPG or X¹; PG is an alcohol protecting group; M is zinc or magnesium; and X and X¹ are independent halide groups. In this preferred embodiment of the first aspect, the nickel(II) catalyst is selected from the group consisting of nickel(II) chloride, nickel(II) chloride hexahydrate, nickel(II) bromide, nickel(II) chloride ethylene glycol dimethyl ether complex, nickel(II) bromide ethylene glycol dimethyl ether complex, nickel(II) acetylacetonate, and nickel(II) acetate tetrahydrate. Preferably, the nickel(II) catalyst is nickel(II) chloride hexahydrate.

In another preferred embodiment of the first aspect, solvent (S1) is selected from the group consisting of methyl t-butyl ether, tetrahydrofuran, 2-methyltetrahydrofuran, toluene, and mixtures thereof.

In a further preferred embodiment of the first aspect, M is magnesium and X is bromide.

In a further preferred embodiment of the first aspect, G is fluoride.

In a further preferred embodiment of the first aspect, the chlorinating agent is selected from the group consisting of chlorine, N-chlorosuccinimide, thionyl chloride, phosphorus trichloride, phosphorus pentachloride, phosphorus oxychloride, hexachloroethane, and 1,3-dichloro-5,5-dimethylhydantoin. Preferably, the chlorinating agent is 1,3-dichloro-5,5-dimethylhydantoin.

In another preferred embodiment of the first aspect, solvent (S2) is selected from the group consisting of methyl t-butyl ether, tetrahydrofuran, 2-methyltetrahydrofuran, toluene, and mixtures thereof. Preferably, solvent (S2) is toluene.

In another preferred embodiment of the first aspect, continuous flow (F1) and continuous flow (F2) are maintained at a temperature in the range of about 50° C. to about 70° C.

In another preferred embodiment of the first aspect, continuous flow (F1) and continuous flow (F2) are combined at an intersection to provide continuous flow (F3) that passes through a plug flow reactor downstream of the intersection.

In another preferred embodiment of the first aspect, the compound of Formula (2-A) is further converted to the compound of Formula (1-A), or a salt thereof. Preferably, the compound of Formula (1-A) is provided as an oxalate salt or a citrate salt.

BRIEF DESCRIPTION OF THE DRAWING

Embodiments of the present invention are described, by way of example only, with reference to the attached FIGURE.

The FIGURE provides a schematic of a continuous flow system used in the processes of the present invention, as Exemplified in Example 1.

DESCRIPTION OF THE INVENTION

The processes of the present invention provide improvements in the preparation of the compound of Formula (2-A), which is an intermediate useful in the preparation of zuclomiphene (1-A), over related batch processes, including enhanced efficiency and selectivity and reduced environmental impact and are therefore more amenable to industrial application.

As used herein, the term "alkyl", alone or as part of another substituent, means, unless otherwise stated, a straight chain, branched chain, or non-aromatic cyclic hydrocarbon radical having the number of carbon atoms designated. When there is no indication of the number of carbon atoms in the alkyl, it is meant, unless otherwise indicated by context, that there are from 1 to 6 carbon atoms. Examples of preferred alkyl groups include methyl, ethyl, n-propyl, iso-propyl, n-butyl, t-butyl, iso-butyl, and sec-butyl.

As used herein, the term "aryl", alone or as part of another substituent, means a polyunsaturated, aromatic, hydrocarbon radical which can comprise one, two or three rings, which are fused together or linked covalently, having the number of ring carbon atoms designated. When there is no indication of the number of carbon atoms in the aryl, it is meant, unless otherwise indicated by context, that there are from 6 to 14 carbon atoms. Examples of preferred aryl groups include phenyl, 4-biphenyl, 9-fluorenyl, 1-naphthyl, 2-naphthyl, 2-anthryl, and 9-anthryl. A preferred aryl group is phenyl.

As used herein, the term "arylalkyl", alone or as part of another substituent, means, unless otherwise stated, an aryl substituent as defined herein attached through an alkyl radical to the parent structure. When there is no indication of the number of carbon atoms in the arylalkyl group, it is meant, unless otherwise indicated by context, that there are from 6 to 14 ring carbon atoms and 1 to 3 carbon atoms in the alkyl portion. Preferred examples of arylalkyl groups include benzyl and phenethyl.

As used herein, the term "substituted" refers to the replacement of one or more hydrogen atoms with a substituent selected from the group consisting of: alkyl, OR, halogen, and $CF_3$. A substituted group may be mono-substituted or polysubstituted. As used herein, each R may be an alkyl group. Preferred examples of substituent groups on substituted aryl groups include methoxy, methyl, fluoride, and chloride.

As used herein, the term "alkyl ether", alone or as part of another substituent, means an alkyl chain bonded to another alkyl or substituted alkyl chain via an oxygen atom wherein alkyl is as defined herein having the number of carbon atoms designated. When there is no indication of the number of carbon atoms in the alkyl ether group, it is meant, unless otherwise indicated by context, that there are from 2 to 6 carbon atoms. Examples of preferred alkyl ether groups include methoxymethyl, methoxyethoxymethyl and 2-tetrahydropyranyl.

As used herein, the term "isomeric purity" refers to the amount of the subject zuclomiphene (or a salt thereof) relative to the total amount of enclomiphene and zuclomiphene (or a salt thereof), expressed as a mole percentage.

As used herein, the term "citrate" refers to the dihydrogen citrate ion that is the counterion in zuclomiphene citrate.

As used herein, "room temperature" generally refers to a temperature of 20-25° C.

As used herein, the term "about" means "close to", and that variation from the exact value that follows the term is within amounts that a person of skill in the art would understand to be reasonable. For example, when the term "about" is used with respect to temperature, a variation of ±5° C. is generally acceptable when carrying out the processes of the present invention. When used with respect to mole equivalents, a variation of ±0.1 moles is generally acceptable.

As used herein, the term "conduit" refers to any compatible pipe, tube, channel, or similar means for conveying fluids or gases in a continuous flow process.

As used herein, the term "residence time" refers to the time required for the subject material to traverse a specified pathway.

As used herein, the term "plug flow reactor", abbreviated "PFR", refers to a flow reactor having a tubular or cylindrical geometry.

In one embodiment of the present invention, zuclomiphene (1-A), or a salt thereof, and intermediates useful in the preparation thereof may be prepared by the process as set out in Scheme 5. Exemplary reagents and conditions for these processes are described herein.

In the processes and compounds of the invention, G is OPG or $X^1$, PG is an alcohol protecting group and $X^1$ is halide.

In the processes and compounds of the invention, PG is an alcohol protecting group. Preferably, PG is a protecting group that is removable in neutral or acidic pH conditions. Preferably, PG is selected from the group consisting of an unsubstituted alkyl group having 1 to 6 carbon atoms, an alkyl ether group having 2 to 6 carbon atoms, a substituted or unsubstituted arylalkyl group having 1 to 3 carbon atoms in the alkyl portion and 6 to 14 ring carbon atoms in the aryl portion, and a SiR'R"R'" group wherein R', and R", R'" are independently selected from the group consisting of an alkyl group having 1 to 4 carbon atoms and a phenyl group. Preferably, PG is selected from the group consisting of methyl, ethyl, n-propyl, isopropyl, n-butyl, sec-butyl, tert-butyl, methoxymethyl, methoxyethoxymethyl, 2-tetrahydropyranyl, benzyl, p-methoxybenzyl, trimethylsilyl, t-butyldimethylsilyl, and triisopropylsilyl. More preferably, PG is selected from the group consisting of methyl, methoxymethyl, 2-tetrahydropyranyl, benzyl, p-methoxybenzyl, and t-butyldimethylsilyl. Most preferably, PG is methyl.

In the processes and compounds of the invention, X' is halide, preferably selected from the group consisting of fluoride, bromide, and iodide, and is most preferably fluoride.

In one embodiment of the present invention, there is provided a process for the preparation of an intermediate of Formula (X):

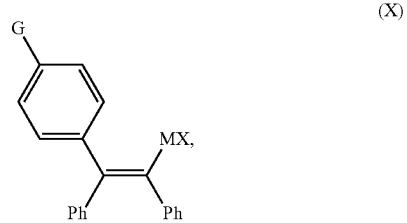

(X)

comprising reacting diphenylacetylene, in the presence of a nickel(II) catalyst and solvent (S1), with a compound of Formula (3-A):

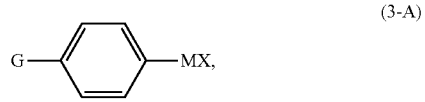

(3-A)

wherein
G is OPG or $X^1$;
PG is an alcohol protecting group;
M is zinc or magnesium; and
X and $X^1$ are independent halide groups.

M is zinc or magnesium, preferably magnesium. X is halide, preferably selected from the group consisting of chloride and bromide. Most preferably, MX is magnesium bromide.

The nickel(II) catalyst may be selected from the group consisting of nickel(II) chloride ($NiCl_2$), nickel(II) chloride hexahydrate ($NiCl_2.6H_2O$), nickel(II) bromide ($NiBr_2$), nickel(II) chloride ethylene glycol dimethyl ether complex ([$NiCl_2$(dme)]), nickel(II) bromide ethylene glycol dimethyl ether complex ([$NiBr_2$(dme)]), nickel(II) acetylacetonate ($Ni(acac)_2$) and nickel(II) acetate tetrahydrate ($Ni(OAc)_2.4H_2O$). Most preferably, the nickel(II) catalyst is nickel(II) chloride ($NiCl_2$) or nickel(II) chloride hexahydrate ($NiCl_2.6H_2O$). The amount of nickel(II) catalyst may be in the range of about 0.1 mol % to about 5 mol %, preferably it is in the range of about 1 mol % and about 3 mol %, with respect to the amount of diphenylacetylene.

The reaction of diphenylacetylene and the compound of Formula (3-A) may be conducted in the presence of a solvent (S1). Solvent (S1) is preferably selected from the group consisting of halogenated hydrocarbons, aromatic hydrocarbons, ethers, and mixtures thereof. More preferably, solvent (S1) is selected from the group consisting of methyl t-butyl ether, tetrahydrofuran, 2-methyltetrahydrofuran, 1,4-dioxane, toluene, and mixtures thereof. Most preferably, solvent (S1) is toluene.

The reaction of diphenylacetylene and the compound of Formula (3-A) may be conducted at any suitable temperature, and is preferably conducted at a temperature in the range of about 20° C. to the boiling point of the reaction mixture. Preferably, the suitable temperature is in the range of about 20° C. to about 30° C.

Compounds of Formula (3-A) wherein M is magnesium and X is halide are commercially available. Alternatively, a compound of Formula (3-A) may be prepared by any desired method including, for example, by reacting the corresponding p-substituted phenyl halide with magnesium or zinc or by lithium-halide exchange of the corresponding p-substituted phenyl halide followed by transmetallation with magnesium halide or zinc halide.

In another embodiment of the present invention, there is provided a continuous flow process for the preparation of a compound of Formula (2-A):

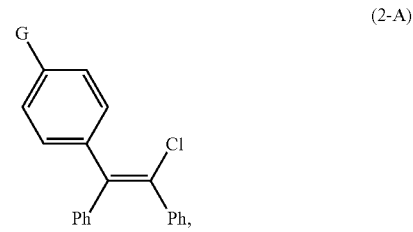

(2-A)

comprising contacting a continuous flow (F1) of the compound of Formula (X):

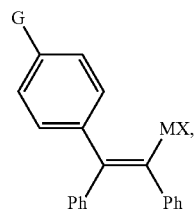

(X)

in a solvent (S1), with a continuous flow (F2) of a chlorinating agent in a solvent (S2), to provide continuous flow (F3) containing the compound of Formula (2-A), wherein G is OPG or $X^1$;
PG is an alcohol protecting group;
M is zinc or magnesium; and
X and $X^1$ are independent halide groups.

In a preferred embodiment of the present invention, the continuous flow process is executed in a continuous flow system having a configuration such as that shown in the FIGURE. In this configuration, the compound of Formula (X) and the chlorinating agent in the respective solvents (S1) and (S2) are provided in respective vessels (V1) and (V2) having associated conduits (C1) and (C2) for the passage of each of the respective reactants as continuous flows (F1) and (F2). The continuous flows (F1) and (F2) combine and provide continuous flow (F3) containing the compound of Formula (2-A). In preferred embodiments of the invention, continuous flow (F3) is collected into a quench tank (Q) prior to the isolation of the compound of Formula (2-A).

In the FIGURE, vessel (V1) is connected by conduit (C1) to a three-way joint (T), where it intersects with conduit (C2), which is connected to vessel (V2). The downstream conduit (C3) from three-way joint (T) is connected to a PFR which feeds to a quenching tank (Q) via conduit (C4).

In a preferred embodiment, the compound of Formula (X) is provided as a reaction mixture resulting from reaction of diphenylacetylene and the compound of Formula (3-A) in solvent (S1) as described herein. Application of a positive nitrogen pressure into vessel (V1) affords a continuous flow (F1) of the reaction mixture containing the compound of Formula (X) through conduit (C1) to the first three-way joint (T), where it mixes with a continuous flow (F2) of the stock preparation of the chlorinating agent pushed from vessel (V2) by nitrogen pressure via conduit (C2) to afford continuous flow (F3). Continuous flow (F3) is pushed through conduit (C3) through a plug flow reactor (PFR) and exits through conduit (C4) into a non-continuous flow quench tank (Q).

In the processes of the present invention, variables related to the execution of the processes are typically optimized by first determining the time required to achieve reaction completion at a given temperature. This reaction time can then be used to establish the necessary residence time, defined as the time it takes to traverse from contact of continuous flows to quench of the reaction components, in the continuous flow system. The volume of the continuous flow system and the prescribed residence time establish the necessary flow rate of (F3), and of the continuous flows (F1) and (F2). Depending upon the choice of reactants, temperatures, and scale of the system, the residence time of the processes of the present invention may be in the range of from seconds to minutes, and is preferably from about 1 second to about 1 minute.

Preferably, the compound of Formula (X) is provided as a reaction mixture resulting from reaction of diphenylacetylene and the compound of Formula (3-A) in solvent (S1) as described herein.

The temperature of continuous flow (F1) is preferably maintained at a temperature to ensure dissolution, preferably in the range of about 20° C. to about 80° C. Preferably, the temperature is maintained in the range of about 50° C. to about 70° C.

The concentration of the compound of Formula X in solvent (S2) in continuous flow (F2) is a practical concentration which maintains good flowability. Preferably, this concentration is from about 0.05 M to about 0.5 M, more preferably between about 0.1 M and about 0.3 M, even more preferably about 0.2 M.

The chlorinating agent may be selected from the group consisting of chlorine ($Cl_2$), N-chlorosuccinimide (NCS), thionyl chloride ($SOCl_2$), phosphorus trichloride (PCIS), phosphorus pentachloride ($PCl_5$), phosphorus oxychloride ($POCl_3$), hexachloroethane, and 1,3-dichloro-5,5-dimethylhydantoin. Preferably, the chlorinating agent is 1,3-dichloro-5,5-dimethylhydantoin.

Depending on the nature of the chlorinating agent, it may be used as is (e.g. gas, liquid) or it may be dissolved in a solvent (S2). The solvent (S2) may be the same or different from the solvent (S1) but is preferably selected from the same group of solvents including halogenated hydrocarbons, aromatic hydrocarbons, ethers, and mixtures thereof. Preferably, solvent (S2) is toluene.

The temperature of continuous flow (F2) is preferably maintained at a temperature to ensure dissolution, preferably in the range of about 20° C. to about 80° C. Preferably, particularly in the case of 1,3-dichloro-5,5-dimethylhydantoin, the temperature is maintained in the range of about 50° C. to about 70° C. to avoid precipitation of the chlorinating agent.

The concentration of the chlorinating agent in solvent (S2) in continuous flow (F2) is a practical concentration which maintains good flowability. Preferably, this concentration is from about 0.2 M to about 0.8 M, more preferably between about 0.4 M and about 0.6 M, even more preferably about 0.5 M.

The optimal flow rate of continuous flows (F1) and (F2) are determined taking into consideration the desired stoichiometry of the reaction, the prescribed residence time, and the total volume of the continuous flow system.

In embodiments, the present invention provides passage of a continuous flow through a conduit. Suitable conduits are any compatible tubing, piping, or channel for transmission of organic solutions. Preferably, a conduit is constructed of material selected from the group consisting of stainless steel, Hastelloy®, perfluoroalkoxy alkanes (PFA), polytetrafluoroethylene (PTFE), high density polyethylene (HDPE), Tygon®, and Norprene®. Suitable inner diameter and length of conduit is selected to permit unobstructed flow of the contents.

The temperature of the flow of reactants in continuous flows (F1) and (F2) and reaction mixture in continuous flow (F3) can be modulated throughout the process as necessary to suit the particular reaction conditions. The temperature of continuous flows (F1) and (F2) is preferably maintained at a temperature to ensure flowability and to avoid unintentional precipitation of solids, preferably in the range of about 50° C. to about 70° C. The continuous flow (F3) is preferably maintained in the range of about 20° C. to about 30° C.

At the end of the reaction, the continuous flow (F3) is collected into a non-continuous flow quenching tank (Q). The quenching solution is any suitable agent capable of quenching reactive organometallic reagents. Preferably, the quenching solution is a dilute acid solution, preferably wherein the acid is selected from the group consisting of mineral acids and organic acids. Preferably, the quenching solution is aqueous ammonium chloride.

In another embodiment of the present invention, there is provided a process for the preparation of zuclomiphene (1-A), or a salt thereof, comprising converting the compound of Formula (2-A) to zuclomiphene (1-A), or salt thereof.

In a preferred embodiment of the conversion, G is fluoride and the compound of Formula (2-A) is a compound of Formula (2-A1):

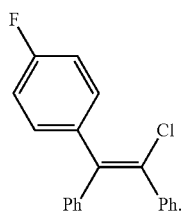

(2-A1)

In this embodiment, the process of converting the compound of Formula (2-A) to zuclomiphene (1-A), or a salt thereof, comprises reacting the compound of Formula (2-A1) with $Et_2NCH_2CH_2OH$ (ie. 2-(N,N-diethylamino)ethanol) in the presence of a base (B1) and a solvent (S3).

The reaction of the compound of Formula (2-A1) with $Et_2NCH_2CH_2OH$ is conducted in the presence of a base (B1). The base (B1) may be any suitable base capable of facilitating an SNAr-type displacement. Preferably, the base (B1) is selected from the group consisting of metal alkoxides and metal hydrides. More preferably, the base (B1) is selected from the group consisting of potassium tert-butoxide, sodium tert-butoxide, sodium hydride, and potassium hydride. Most preferably the base (B1) is potassium tert-butoxide.

The reaction of the compound of Formula (2-A1) with $Et_2NCH_2CH_2OH$ is conducted in the presence of a solvent (S3). Preferably, the solvent (S3) is selected from the group consisting of ethers, sulfoxides, and amides. More preferably, the solvent (S3) is selected from the group consisting of dimethyl sulfoxide, N,N-dimethylformamide, tetrahydrofuran, 2-methyltetrahydrofuran and 1,4-dioxane. Most preferably, the solvent (S3) is 1,4-dioxane.

The reaction of the compound of Formula (2-A1) with $Et_2NCH_2CH_2OH$ may be conducted at any suitable temperature, and is preferably conducted at or near the boiling point of the reaction mixture. Most preferably, the suitable temperature is in the range of about 70° C. to about 110° C.

In another embodiment of the conversion, G is chloride, bromide, or iodide and the compound of Formula (2-A) is a compound of Formula (2-A2):

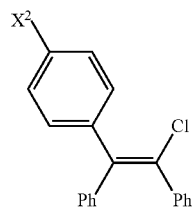

(2-A2)

wherein $X^2$ is chloride, bromide or iodide. In this embodiment, the process of converting the compound of Formula (2-A) to zuclomiphene (1-A), or a salt thereof, comprises reacting the compound of Formula (2-A2) with $Et_2NCH_2CH_2OH$ in the presence of a copper catalyst and a base (B2).

The reaction of the compound of Formula (2-A2) with $Et_2NCH_2CH_2OH$ is conducted in the presence of a copper catalyst, preferably selected from the group consisting of copper(I) chloride, copper(I) bromide, copper(I) iodide, copper(I) oxide, copper(I) acetate, copper(I) thiocyanate, and copper(I) sulfide, and is most preferably copper(I) iodide. Preferably, the amount of copper catalyst relative to the amount of the compound of Formula (2-A2) is between about 1 mol % and about 30 mol %, and is most preferably between about 10 mol % and about 25 mol %.

In the reaction of the compound of Formula (2-A2) with $Et_2NCH_2CH_2OH$, an excess amount of $Et_2NCH_2CH_2OH$ can also function as a base. Alternatively, the reaction may be conducted in the presence of a base (B2) that is preferably selected from the group consisting of tertiary amines, metal carbonates, and metal bicarbonates. Preferably, base (B2) is selected from the group consisting of sodium carbonate, sodium bicarbonate, potassium carbonate, potassium bicarbonate, lithium carbonate, triethylamine, and diisopropylethylamine. Most preferably, base (B2) is selected from the group consisting of triethylamine, potassium carbonate, and mixtures thereof.

The reaction of the compound of Formula (2-A2) with $Et_2NCH_2CH_2OH$ may be conducted in the presence of a solvent (S4), preferably a high-boiling solvent selected from the group consisting of ethers, aromatic hydrocarbons, amides, and nitriles. More preferably, the solvent (S4) is selected from the group consisting of 1,4-dioxane, toluene, N,N-dimethylformamide and acetonitrile.

The reaction of the compound of Formula (2-A2) with $Et_2NCH_2CH_2OH$ may be conducted at any suitable temperature, and is preferably conducted at or near the boiling point of the reaction mixture. Most preferably, the suitable temperature is in the range of about 80° C. to about 130° C.

In another embodiment of the conversion, G is OPG and the compound of Formula (2-A) is a compound of Formula (2-A3):

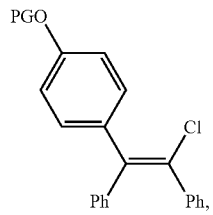

(2-A3)

wherein PG is an alcohol protecting group. In this embodiment, the process of converting the compound of Formula (2-A) to zuclomiphene (1-A), or a salt thereof, comprises deprotecting the compound of Formula (2-A3) and alkylating the resulting intermediate with a compound of Formula $Et_2NCH_2CH_2LG$, or a salt thereof, wherein LG is a leaving group.

Preferably, PG in the compound of Formula (2-A3) is a protecting group that is removable in neutral or acidic pH conditions in order to avoid any isomerization of the double bond that may occur as a result of exposure to basic pH conditions. Preferably, PG is a protecting group that is removable by treatment with an acid (A1), which may be any suitable Lewis or Brønsted acid. Preferably, acid (A1) is selected from the group consisting of boron tribromide ($BBr_3$), trimethylsilyl iodide (TMSI), trimethylsilyl chloride (TMSCI), aluminum chloride ($AlCl_3$), tin(IV) chloride ($SnCl_4$), titanium tetrachloride ($TiCl_4$), hydrochloric acid, and tetrabutylammonium fluoride (TBAF). Most preferably, acid (A1) is boron tribromide ($BBr_3$).

The deprotection of the compound of Formula (2-A3) may be conducted in the presence of a solvent (S5), preferably selected from the group consisting of halogenated hydrocarbons and ethers. More preferably, the solvent (S5) is selected from the group consisting of dichloromethane and methyl t-butyl ether. Most preferably, the solvent (S5) is dichloromethane.

The deprotection of the compound of Formula (2-A3) may be conducted at any suitable temperature, and is preferably conducted at sub-zero temperatures. More preferably, the suitable temperature is between about −80° C. and about 0° C. Most preferably, the suitable temperature is between about −80° C. and about −40° C.

In an embodiment, the product of deprotecting the compound of Formula (2-A3) is a compound of Formula (1-int):

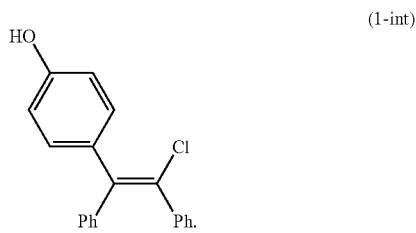 [SMILES: Oc1ccc(/C(=C(\Cl)c2ccccc2)c2ccccc2)cc1]

(1-int)

Intermediate (1-int) may be isolated in the processes of the present invention or it may be used in situ without isolation.

In the alkylation reaction, LG in the compound of Formula $Et_2NCH_2CH_2LG$ is a leaving group, preferably selected from the group consisting of halide and a sulfonate. Preferred sulfonates are selected from methanesulfonate, toluenesulfonate, and trifluoromethanesulfonate. Preferably, LG is halide selected from the group consisting of chloride, bromide and iodide, and is most preferably chloride. Preferably, the compound of Formula $Et_2NCH_2CH_2LG$ is provided as a salt such as a hydrochloride salt, which is neutralised for the reaction. Neutralisation of a salt of $Et_2NCH_2CH_2LG$ may lead to formation of the corresponding aziridinium ion of this compound, which may be the active species in the reaction.

The alkylation reaction is preferably conducted in the presence of a base (B3). Base (B3) is preferably selected from the group consisting of metal carbonates, metal bicarbonates, and metal hydroxides. Preferably, base (B3) is selected from the group consisting of potassium carbonate, cesium carbonate, sodium carbonate, potassium hydroxide, and sodium hydroxide. Most preferably, the base (B3) is cesium carbonate.

The alkylation reaction may be conducted using phase-transfer conditions to avoid prolonged contact of the compound of Formula (1-int) to strong basic conditions such as when using sodium hydroxide. A suitable phase-transfer catalyst is selected from the group consisting of tetrabutylammonium bromide, benzyltriethylammonium chloride, and methyltributylammonium chloride. Preferably, the phase transfer catalyst is benzyltriethylammonium chloride.

The alkylation reaction may be conducted in the presence of a solvent (S6), preferably selected from the group consisting of ketones, amides, and alcohols. More preferably, the solvent (S6) is selected from the group consisting of acetone, N,N-dimethylformamide, and ethanol. Most preferably, the solvent (S6) is N,N-dimethylformamide The alkylation reaction may be conducted at any suitable temperature, and is preferably conducted at a temperature in the range of about 30° C. to the boiling point of the reaction mixture. More preferably, the temperature is in the range of about 40° C. and about 80° C.

Preferably, the reaction of diphenylacetylene with the compound of Formula (3-A) is stereoselective in favour of the Z-configuration. Preferably, the isomeric composition of zuclomiphene (1-A) or the compound of Formula (2-A) that is produced is enriched in the Z-isomer relative to the E-isomer. Preferably, the isomeric purity of the zuclomiphene (1-A) or the compound of Formula (2-A) that is produced is at least about 60%, more preferably the isomeric purity is at least about 80%. Even more preferably, the isomeric purity of the zuclomiphene (1-A) or the compound of Formula (2-A) that is produced is at least about 90%, most preferably, the isomeric purity is at least about 95%.

The zuclomiphene (1-A), or a salt thereof, that is provided may be subjected to further purification steps to increase the chemical and/or isomeric purity. Preferably, purification comprises crystallization of a salt of zuclomiphene (1-A) from a suitable solvent. A suitable salt is derived from an acid (HA) which may bear one or more acidic protons and is preferably selected from the group consisting of oxalic acid, binaphthyl hydrogen phosphate, D,L-aspartic acid, cyclamic acid, fumaric acid, L-glutamic acid, hippuric acid, L-malic acid, malonic acid, nicotinic acid, di-p-toluoyl-D-tartaric acid, saccharin, D-tartaric acid, and citric acid. Preferably, the acid (HA) is oxalic acid or citric acid and the molar ratio of zuclomiphene to acid (HA) is about 1:1.

EXAMPLES

Comparative Example 1: Preparation of (Z)-4-(2-chloro-1,2-diphenylethenyl)fluorobenzene (Compound of Formula (2-A1)) Using a Batch System

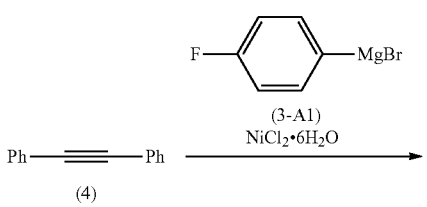

-continued

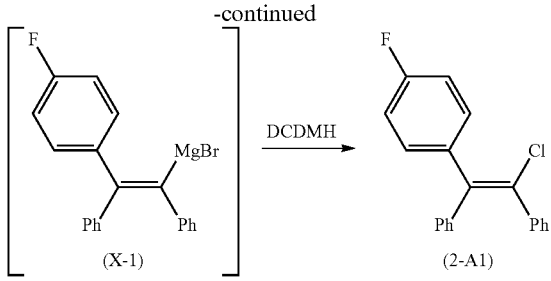

A mixture of 4-fluorophenylmagnesium bromide in tetrahydrofuran (79 mL, 78.55 mmol), diphenylacetylene (10.00 g, 56.11 mmol), and nickel(II) chloride hexahydrate (0.27 g, 1.12 mmol, 2 mol %) in dry toluene (250 mL) was stirred at room temperature until all of the diphenylacetylene was consumed as confirmed by $^1$H NMR (CDCl$_3$) (3.5 hours). This reaction mixture was then transferred to a suspension of 1,3-dichloro-5,5-dimethyl-hydantoin (27.60 g, 140.30 mmol) in toluene (100 mL) via canula over 25 minutes. After stirring for a further hour at room temperature, the reaction mixture was cooled to 5-10° C. and a saturated aqueous solution of ammonium chloride (100 mL) was added. The solution was diluted with water (50 mL) to dissolve any solids and the phases were separated. The organic phase was washed with water (150 mL), stirred over Na$_2$SO$_4$, filtered, and stirred with a saturated aqueous solution of Na$_2$S$_2$O$_3$ (100 mL). The aqueous phase was removed and the organic phase was washed with water (100 mL) before concentrating in vacuo to 50 mL. Heptanes (200 mL) was charged and the solution was filtered through glass microfiber affording a suspension. The suspension was stirred at room temperature for 4 hours prior to filtration to afford a solid (4.32 g) having HPLC purity of 79 a % (21 a % impurity (IMP)).

The following examples are illustrative of some of the embodiments of the invention described herein. It will be apparent to the person skilled in the art that various alterations to the described processes in respect of the reactants, reagents, and conditions may be made when using the processes of the present invention without departing from the scope or intent thereof.

Example 1: Preparation of (Z)-4-(2-chloro-1,2-diphenylethenyl)fluorobenzene (Compound of Formula (2-A1)) Using a Continuous Flow System

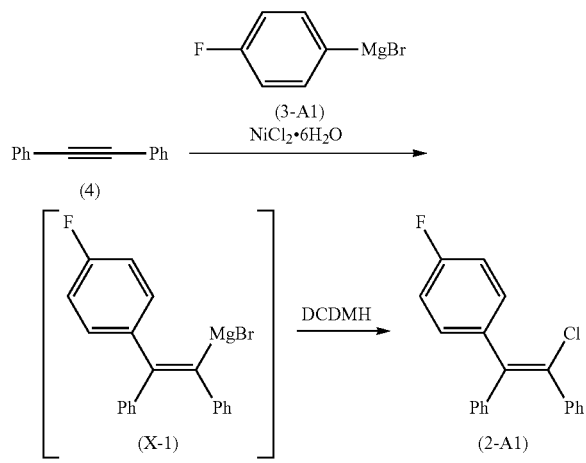

A. Preparation of the Intermediate of Formula (X-1) Feed Solution

A mixture of 4-fluorophenylmagnesium bromide in tetrahydrofuran (29.2 mL, 29.18 mmol), diphenylacetylene (4.00 g, 22.44 mmol), and nickel(II) chloride hexahydrate (0.11 g, 0.45 mmol, 2 mol %) in dry toluene (80 mL) was stirred at room temperature until all of the diphenylacetylene was consumed as confirmed by $^1$H NMR in CDCl$_3$ (3 hours). The resulting solution containing the intermediate of Formula (X-1) was transferred via cannula to an HPLC solvent bottle rated for pressure up to 25 psi (V1) fitted with a lid.

B. Preparation of the 1,3-dichloro-5,5-dimethyl-hydantoin Feed Solution 1,3-dichloro-5,5-dimethyl-hydantoin (11.05 g, 56.11 mmol) was dissolved in dry toluene (102.2 mL) at 60° C. and the solution was transferred via cannula to an HPLC solvent bottle rated for pressure up to 25 psi (V2) fitted with a lid.

C. Preparation of the Compound of Formula (2-A1)

A continuous flow process was conducted in a system (depicted in the FIGURE) comprised of tubing (conduits), a three-way joint, a plug flow reactor (PFR) having a working volume of 2 mL, and a quench flask (Q). (V1) and (V2), containing the feed solutions of the compound of Formula (X) and 1,3-dichloro-5,5-dimethyl-hydantoin, were connected to a three-way joint (T) via conduits (C1) and (C2), respectively. The conduit (C3) from the three-way joint (T) was connected downstream to plug flow reactor (PFR), which was connected to quench flask (Q) by conduit (C4). (V1) and (V2) were immersed in oil baths to maintain the required temperature throughout the process. (V1) and (V2) were further connected to a nitrogen source via respective conduits (CN1) and (CN2). Nitrogen flow and pressure through the conduits (CN1) and (CN2) was controlled by respective valves (VV1) and (VV2) and pressure regulators (R1) and (R2). The conduits and plug flow reactor were constructed of perfluoroalkoxy tubing with an ⅛" OD and had a ¹⁄₁₆" ID. The valves were constructed of polyether ether ketone (PEEK) and had a ⅛" ID. The three-way joint was contructed of PEEK and had a ⅛" ID with a 0.05" through-hole.

The feed solutions of the compound of Formula (X1) and 1,3-dichloro-5,5-dimethyl-hydantoin were maintained at about 60° C. by submerging each vessel (V1) and (V2) into an oil bath. The flow rate of each solution was controlled by passing nitrogen gas regulated at a pressure of about 10 psi through open valves (VV1) and (VV2) into vessels (V1) and (V2) thereby pushing each respective solution through the corresponding conduit. The respective flows (F1) and (F2) were combined in joint (T) to afford flow (F3) which passed via (C3) into (PFR) and was quenched into flask (Q) via (C4). The temperature of the plug flow reactor (PFR) was maintained at room temperature throughout.

The continuous flow (F4) passed from (PFR) into quench flask (Q) containing a saturated aqueous NH4Cl solution (48 mL). At the set pressure and working volume, the residence time of the process was about 2 minutes. Following consumption of the feed solutions in (V1) and (V2), the flasks were replenished with toluene, which was pumped through the system from each respective flask for 5 minutes at the established flow rates. The combined rinses were collected in quench flask (Q) together with the reaction mixture.

The resulting biphasic solution was separated and the organic phase was poured into an aqueous Na$_2$S$_2$O$_3$ solution (5.3 g Na$_2$S$_2$O$_3$/48 mL water, 33.67 mmol), which was maintained at 0-5° C. Following brief stirring, the biphasic solution was separated, and the organic phase was washed with water (48 mL), 5% aqueous NaOH (48 mL) and brine (48 mL). Finally, the organic phase was filtered through diatomaceous earth and Na$_2$SO$_4$, and the cake was washed with methyl t-butyl ether (10 mL). The clear organic solution was concentrated in vacuo to afford an oil, which was further dried in vacuo at room temperature to afford the compound of Formula (2-A1) (quantitative yield). This crude material was purified in ethanol (8 mL) to afford the compound of Formula (2-A1) (3.48 g, 50.2% yield) having an having an HPLC purity of 94.13 a % (4.88 a % impurity (IMP)).

Example 2: Preparation of zuclomiphene (1-A) oxalate from the Compound of Formula (2-A1)

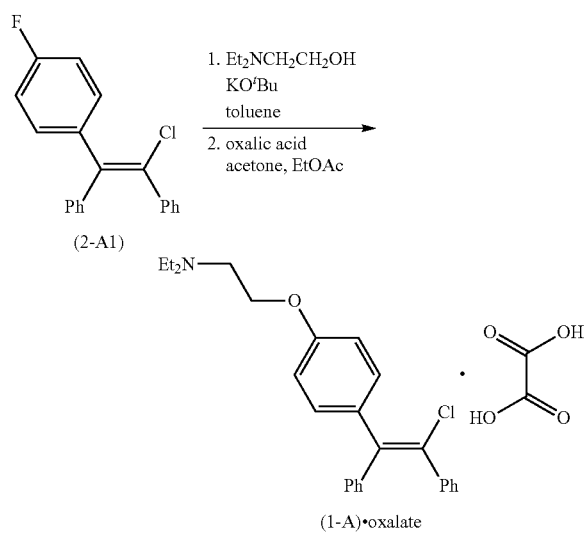

A mixture of potassium tert-butoxide (1.09 g, 9.72 mmol) and 2-(N,N-diethylamino)ethanol (1.4 mL, 10.36 mmol) in toluene (10 mL) was dissolved by heating to 100° C. for about 10 minutes. The compound of Formula (2-A1) (2.0 g, 6.48 mmol) prepared in accordance with Example 1 was added and the reaction mixture was stirred overnight at 100° C. $^1$H NMR (CDCl$_3$) showed reaction completion and the reaction mixture was charged into saturated aqueous ammonium chloride solution and extracted with methyl t-butyl ether. The organic phase was concentrated to dryness in vacuo to afford zuclomiphene (1-A) as an oil (2.35 g, 89.4% yield) having an HPLC purity of 91.78 a %.

A mixture of the oil (2.35 g, 6.48 mmol), oxalic acid (0.82 g, 6.48 mmol), acetone (20 mL), and ethyl acetate (20 mL) was stirred at 50° C. for two hours. The resulting solution was cooled to room temperature for 20 minutes and then to 0-5° C. for one hour. The suspension was filtered, washed with an acetone/ethyl acetate mixture (10 mL), and the cake dried overnight in vacuo at room temperature to afford zuclomiphene (1-A) oxalate as a white solid (1.94 g, 60.4% yield) having an HPLC purity of 98.11 a %.

What is claimed is:

1. A continuous flow process for the preparation of a compound of Formula (2-A):

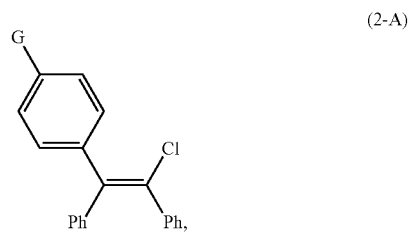

comprising contacting a continuous flow (F1) of the compound of Formula (X):

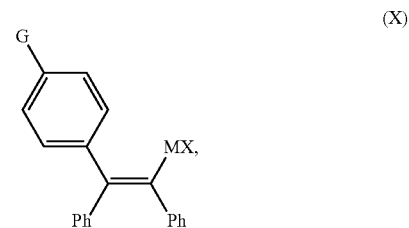

in a solvent (S1), with a continuous flow (F2) of a chlorinating agent in a solvent (S2), to provide continuous flow (F3) containing the compound of Formula (2-A),
wherein
G is OPG or X$^1$;
PG is an alcohol protecting group;
M is zinc or magnesium; and
X and X$^1$ are independent halide groups.

2. The continuous flow process of claim 1, wherein the continuous flow (F1) of the compound of Formula (X) comprises a reaction mixture resulting from reacting diphenylacetylene, in the presence of a nickel(II) catalyst and solvent (S1), with a compound of Formula (3-A):

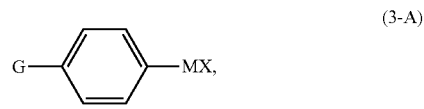

wherein
G is OPG or X$^1$;
PG is an alcohol protecting group;
M is zinc or magnesium; and
X and X$^1$ are independent halide groups.

3. The continuous flow process of claim 2, wherein the nickel(II) catalyst is selected from the group consisting of nickel(II) chloride, nickel(II) chloride hexahydrate, nickel(II) bromide, nickel(II) chloride ethylene glycol dimethyl ether complex, nickel(II) bromide ethylene glycol dimethyl ether complex, nickel(II) acetylacetonate, and nickel(II) acetate tetrahydrate.

4. The continuous flow process of claim 3, wherein the nickel(II) catalyst is nickel(II) chloride hexahydrate.

5. The continuous flow process of claim 3, wherein solvent (S1) is selected from the group consisting of methyl t-butyl ether, tetrahydrofuran, 2-methyltetrahydrofuran, toluene, and mixtures thereof.

6. The continuous flow process of claim 1, wherein M is magnesium and X is bromide.

7. The continuous flow process of claim 6, wherein G is fluoride.

8. The continuous flow process of claim 7, wherein the chlorinating agent is selected from the group consisting of chlorine, N-chlorosuccinimide, thionyl chloride, phosphorus trichloride, phosphorus pentachloride, phosphorus oxychloride, hexachloroethane, and 1,3-dichloro-5,5-dimethylhydantoin.

9. The continuous flow process of claim 8, wherein the chlorinating agent is 1,3-dichloro-5,5-dimethylhydantoin.

10. The continuous flow process of claim 9, wherein solvent (S2) is selected from the group consisting of methyl t-butyl ether, tetrahydrofuran, 2-methyltetrahydrofuran, toluene, and mixtures thereof.

11. The continuous flow process of claim 10, wherein the solvent (S2) is toluene.

12. The continuous flow process of claim 7, wherein continuous flow (F1) and continuous flow (F2) are maintained at a temperature in the range of about 50° C. to about 70° C.

13. The continuous flow process of claim 1, wherein continuous flow (F1) and continuous flow (F2) are combined at an intersection to provide continuous flow (F3) that passes through a plug flow reactor downstream of the intersection.

14. The continuous flow process of claim 1, wherein the compound of Formula (2-A) is further converted to the compound of Formula (1-A):

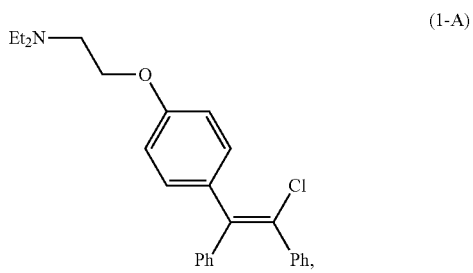

(1-A)

or a salt thereof.

15. The continuous flow process of claim 14, wherein the compound of Formula (1-A) is provided as an oxalate salt.

16. The continuous flow process of claim 14, wherein the compound of Formula (1-A) is provided as a citrate salt.

* * * * *